United States Patent [19]
Buser et al.

[11] Patent Number: 5,821,317
[45] Date of Patent: Oct. 13, 1998

[54] ADDUCT OF BISEPOXY COMPOUND AND P GUANAMINE

[75] Inventors: Antonius Johannes Wilhelmus Buser, Wehl; Jan Andre Jozef Schutyser, Dieren, both of Netherlands

[73] Assignee: Akzo Nobel NV, Arnhem, Netherlands

[21] Appl. No.: 910,640

[22] Filed: Aug. 13, 1997

Related U.S. Application Data

[60] Provisional application No. 60/042,346, Mar. 24, 1997.

[30] Foreign Application Priority Data

Aug. 23, 1996 [NL] Netherlands .......................... 1003864

[51] Int. Cl.⁶ .................................................. C08G 59/68
[52] U.S. Cl. .............................. 528/89; 528/94; 528/103; 528/118; 525/504; 525/506; 525/525; 525/538; 428/901
[58] Field of Search ................................ 528/89, 94, 103, 528/118; 525/504, 506, 525, 538; 428/901

[56] References Cited

U.S. PATENT DOCUMENTS

| | | | |
|---|---|---|---|
| 3,876,635 | 4/1975 | Deiner et al. | 260/249.9 |
| 4,086,206 | 4/1978 | Saito et al. | 260/45.8 |
| 5,534,573 | 7/1996 | Leake | 524/100 |

FOREIGN PATENT DOCUMENTS

| | | | |
|---|---|---|---|
| 2 126 880 | 11/1972 | Germany | C07D 55/20 |
| 1343022 | 1/1974 | United Kingdom | C07F 9/40 |
| WO 93/11176 | 6/1993 | WIPO | C08F 283/10 |

OTHER PUBLICATIONS

Dutch Search Report for NL 1003864 dated Apr. 29, 1997.

*Primary Examiner*—Randy Gulakowski
*Attorney, Agent, or Firm*—Loretta A. Miraglia; Louis A. Morris

[57] ABSTRACT

The invention pertains to an adduct obtainable by condensation of a bisepoxy compound and a P-guanamine according to the formula

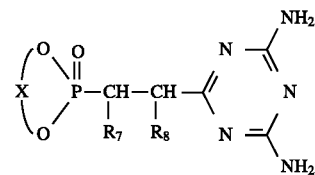

wherein X is $CR_3R_4$—$(CR_1R_2)_n$—$CR_5R_6$ or o-phenylidene, n is 0 or 1, and $R_1$–$R_8$ may be the same or different and represent H, methyl or ethyl, and the molar ratio P-guanamine: bisepoxide is 0.60 to 0.35. The adduct is used in the manufacture of synthetic materials, notably printed wiring boards (PWBs).

13 Claims, No Drawings

ADDUCT OF BISEPOXY COMPOUND AND P GUANAMINE

This application claims the benefit of provisional application 60/042,346 filed on Mar. 24, 1997.

The present invention pertains to an adduct of a bisepoxy compound and a P-guanamine, the use of such an adduct in a resin formulation, in synthetic materials, and in particular in printed wiring boards (PWBs), and to the synthetic materials and PWBs thus obtained.

BACKGROUND OF THE INVENTION

The laminates for PWBs according to the prior art, reinforced with glass and containing epoxy, have generally been rendered flame retardant by the use of brominated compounds. For instance, the most commonly employed FR-4 laminate contains an epoxy resin prepared by reacting tetrabromobisphenol A with an excess of diglycidyl ether of bisphenol A.

In reinforced as well as non-reinforced synthetic materials, the drawback to using brominated, flame extinguishing compounds lies in their harmful effect on the environment. Fires and uncontrolled combustion in ovens may cause the extremely toxic dioxin to be formed.

For that reason there is need for bromine-free epoxy resins which constitute a proper alternative to the present bromine-containing epoxy resins as far as processing and flame retardant properties are concerned. Flame retardance can be achieved in an alternative manner by the chemical incorporation of suitable phosphorous and nitrogenous compounds into resin formulations, as is disclosed, int. al., in PCT/EP92102705. In this patent application interpenetrating polymer network (IPN) technology is used to introduce a phosphorous epoxy resin via the first network and triallyl-(iso)cyanurate polymerizable under the influence of radicals via the second network.

German patent application 2,126,880 describes the preparation and suitability for use as hardener in epoxy resins of $\Omega$-dialkoxy- or $\Omega$-alkylenedioxy-phosphinyl-alkyl-guanamines, compounds which contain acyclic and cyclic phosphonate ester groups, respectively. These guanamines are flame retardant materials for cured epoxy systems. The suitability of such systems when used in laminates, notably those employed as PWB-substrates, was not explored in this document. GB patent specification 1,343,022, discloses $\beta$-(dialkoxyphosphinyl)-ethyl-guanamines used to impart flame resistance to amino resins suitable for treating paper, textiles, wood, and laminates.

SUMMARY OF THE INVENTION

It was found that not all phosphorous guanamines (henceforth referred to by the abbreviation P-guanamine) are suited to be used for curing or incorporation into bisepoxy compounds, and that some P-guanamines even are wholly unsuitable for use in electrolaminates.

Now, a highly suitable adduct has been found which can be obtained by the condensation of a bisepoxy compound and a P-guanamine according to FIG. 1:

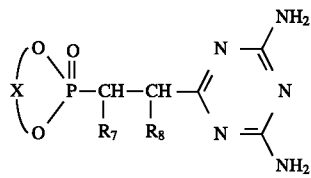

wherein X is $CR_3R_4$—$(CR_1R_2)_n$—$CR5R_6$ or o-phenylidene, n is 0 or 1, and $R_1$–$R_8$ may be the same or different and represent H, methyl or ethyl, and the molar ratio P-guanamine: bisepoxide is 0.60 to 0.35.

Having the proper P-guanamine: bisepoxide molar ratio is a prerequisite in this case, since the adducts will not give favorable results except within the limits set above.

DETAILED DESCRIPTION OF THE INVENTION

Suitable P-guanamines after being cured with epoxides give products which have a stable glass transition temperature (Tg) and produce only a small quantity of volatile substances at 300° C. At present, it is customary in the electronics industry to make a solution of epoxy resin formulation and glass cloth into prepregs in a drying tower at a maximum temperature of 185° C. in not more than 2 hours. Stacked prepregs provided with copper foil on both sides are thereafter pressed to a laminate at a maximum temperature of 185° C. for maximally 2 hours. Industrially made laminate has to have stable thermal properties, which are measured as prescribed by electronics industry (e.g., the IPC TM-650 methods of The Institute for Interconnecting and Packaging of Electronic Circuits).

These thermal properties are crucial when it comes to processing the laminate into PWBs, loading the PWB with components, and the service properties of the PWB in electronic equipment. For instance, during soldering the laminate has to be able to withstand a thermal shock of 288° C. without the copper traces being delaminated. In this case it is of the essence that the laminate neither contains or generates any volatile substances nor displays significant shrinkage. Modern laminates for that reason will show a constant Tg when measurements are carried out in accordance with standard thermal analysis techniques such as DSC (differential scanning calorimetry) or TMA (thermomechanical analysis) in the range of 20° to 250° C. Also, the resin in commercial laminates when measured by TGA (thermo-gravimetric analysis) at 300° C. may not lose more than 5% (w/w) of volatile substance.

The P-guanamines according to the invention display a stable Tg on being cured and lose only a small quantity of volatile substance at 300° C. The well-known $\Omega$-(dialkoxyphosphinyl)-alkyl-guanamines do not display these properties and are not suitable for use for that reason.

In general, P-guanamines are polar molecules which are poorly soluble in conventional solvents such as acetone and methylethyl ketone (MEK) at room temperature. Their solubility in commercially available epoxy resins such as the diglycidyl ether of bisphenol A likewise is insufficient, making it impossible to prepare solvent-free formulations at room temperature. Polar solvents such as alcohols (e.g., 1-methoxy-2-propanol) constitute an improvement, yet are not sufficiently suitable as solvents in resin formulations having a solids content of 50 to 70% where the epoxy resin is mixed with the P-guanamine in virtually stoichiometric ratio. It should be noted in this context that the P-guanamine has two amino groups and so is capable of reacting as a tetrafunctional molecule with four epoxy groups. In the present invention it was found that the P-guanamine after reaction in a melt or in solution (e.g., in 1-methoxy-2-propanol) with the diglycidyl ether of bisphenol A provides a clear, homogeneous, solid adduct which is readily soluble in mixtures of MEK and 1-methoxy-2-propanol. This is under the condition that the molar ratio tetrafunctional P-guanamine: bisepoxide does not exceed 0.60 and the gelling time for the adduct having a minimum molar ratio of 0.35 measured on a hot plate at 171° C. is not more than 12 minutes. In this way it is ensured that most of the P-guanamine will react with at least one molecule of bisepoxide and become soluble as a result. Such an adduct in addition to epoxy groups contains amino groups and is readily curable in the presence of catalysts such as 2-methyl imidazole under standard conditions. At a molar ratio of 0.60 at the most there will be no signs of phase separation in the cured resin at elevated temperature (>171° C.). Such phase separation does occur in the case of molar ratios higher than 0.60.

The cyclic phosphonate esters are 5-membered rings (dioxaphospholane; n=0) or 6-membered rings (dioxaphosphorinane; n=1). In view of the 6-membered rings having greater thermal stability, preference is given to adducts having a P-guanamine according to Formula I, wherein n is 1. In particular, preference is given to P-guanamines according to Formula I, wherein $R_1$ and $R_2$ are both methyl groups and $R_3$–$R_8$ are H. More preferably still, the P-guanamine is (5,5-dimethyl-2-oxo-1,3,2-dioxaphosphorinanyl)-ethyl-guanamine. This compound, synthesized by a route analogous to that described in DP 2,126,880, is a solid compound having a high melting point (220° C.) and a volatility of 4% at 300° C. (TGA measurement). By contrast, the well-known β-diethoxyphosphinyl-ethyl-guanamine melts at 165° C. and gives 16% of volatile substance at 300° C.

The epoxy resin composition as used in electrolaminate contains
an adduct according to the invention
optionally, other epoxy resins
optionally, a hardener
optionally, a catalyst.

The adducts can be prepared in conventional manners. One suitable way of preparing the adduct according to the invention is to melt condense P-guanamine and bisepoxy compound with or without a solvent being present, with the molar ratio P-guanamine: bisepoxide being 0.60 to 0.35.

At a molar ratio of 0.35 the gelling time measured at 171° C. is not more than 12 minutes. Suitable difunctional epoxy resins are prepared, e.g., by reacting aromatic dihydroxy compounds such as bisphenol A, bisphenol S (sulphone bisphenol), and bisphenol F (methylene bisphenol with epichlorohydrin). One example is the diglycidyl ether of bisphenol A, which is commercially available as "EPIKOTE®" 828. Also suitable are cycloaliphatic bisepoxides such as 3,4-epoxy-cyclohexylmethyl-3,4-epoxycyclohexane carboxylate.

The adduct is prepared in the melt at a temperature in the range of 120 to 180° C., preferably 135° to 175° C. In solution, at a total solids content of 50 to 80% of epoxy resin and P-guanamine, the reaction is carried out in polar solvents such as alcohols, alcohol ethers or dimethyl formamide. For the effective production of adducts at a temperature of about 130° C., 1-methoxy-2-propanol in particular was found to be useful.

Examples of other epoxy resins which may be added during the resin formulation are phenol type epoxy resins, such as those based on the diglycidyl ether of bisphenol A, polyglycidyl ethers of phenol-formaldehyde novolak or cresol-formaldehyde novolak. Other epoxy resins are based on the triglycidyl ether of tris-(p-hydroxyphenol)methane or on the tetraglycidyl ether of tetraphenyl ethane. Also suitable are epoxy resins of the amine type, such as those based on tetraglycidyl methylene diphenyl diamine or triglycidyl isocyanurate, and epoxy resins of the cycloaliphatic type, such as those based on 3,4-epoxycyclohexylmethyl-3,4-epoxycyclohexane carboxylate. The term "epoxy resin" also encompasses the reaction products of an excess of epoxy-containing compound (e.g., of the types indicated above) and aromatic dihydro compounds.

Although as a result of the presence of NH-groups and epoxy groups the adduct is self-curing, it may be advisable to use an extra hardener for stoichiometric reasons or because of the product properties. Hardeners such as polyhydric phenol, cyclic anhydrides, and amines may be employed in these cases. Examples of polyhydric aromatic compounds are phenol/formaldehyde and cresol/formaldehyde novolak resins, as well as resorcinol, bisphenol A, and sulphone diphenol. Examples of cyclic anhydrides are aromatic anhydrides such as phthalic anhydride, tetrabromophthalic anhydride; cycloaliphatic anhydrides such as hexahydrophthalic anhydride; copolymers of maleic anhydride and styrene. Examples of amines are dicyanodiamide, diphenyl guanidine, benzoguanamine, and aromatic amines such as methylene dianiline.

Suitable catalysts include imidazoles, more particularly alkyl-substituted imidazoles such as 2-methyl imidazole and 2-ethyl-4-methyl imidazole, and tertiary amines such as benzyl dimethyl amine. Also useful are cationic catalysts such as boron trifluoride-ethyl amine complex.

The quantity in which such a catalyst is employed is dependent on the chemical composition of the resin formulation, but is generally in the range of 0.01 to 5 per cent by weight, calculated on the overall weight of the solid resin components.

In general, organic solvents are employed in the preparation of the resins according to the invention. Suitable solvent combinations are those of glycol ethers such as propylene glycol monomethyl ether and/or dimethyl formamide and ketones such as methylethyl ketone and acetone.

Laminates to be used in the electronics industry (notably for PWBs) are generally manufactured by impregnating a supporting or reinforcing fabric with a resin and then partially curing the resin. Such an impregnated fabric is commonly referred to as a prepreg. Several prepregs together with one or more layers of copper laminated with heat and pressure will give an electrolaminate which can be made into a PWB by means of well-known printing and etching techniques.

The resins according to the invention are suitable for impregnating, say, fabric, unidirectionally laid bundles, and cloth made of a wide range of materials such as glass, quartz, carbon, aramid, and boron fibres. They are particularly suited to be used in the manufacture of electrolaminates.

Also, the resins according to the invention can be used in glue, coating, potting resin, embedding resin, encapsulating resin, sheet moulding compound, and bulk moulding compound.

In addition to their aforementioned use as composites for electro-laminates, the resins according to the invention can be employed to make composites for, say, the construction, aviation, and motor industries. Structural composites suitable for this purpose can be made in a known manner, e.g., by impregnating reinforcing material with molten or dissolved resin or by means of resin transfer moulding, filament winding, pultrusion or RIM (reaction injection moulding). The usual additives may be added to the resins according to the invention, e.g., dyes, pigments, thixotropic agents, flow regulators, and stabilizers. If so desired, additional inorganic solid flame extinguishers such as aluminum trihydrate or magnesium hydroxide and organic solid or liquid flame extinguishers such as salt of melamine with phosphoric acid or aromatic phosphonate oligomers may be added to further enhance the flame retardant properties.

Furthermore, Ω-(alkylenedioxy-phosphinyl)-alkyl guanamines employed as solid matter in thermoplasts such as polyamides or in reinforced synthetic materials can serve successfully as flame retardant additive. The adduct according to the invention has the advantage that P-guanamine is not a salt and the additives, if any, do not have a negative effect on the electric properties of the synthetic material. Also, the P-guanamines according to the invention have a higher thermal stability than the melamine phosphoric acid salt and so are less likely to lead to destruction of the flame extinguisher on processing (e.g., through injection moulding) and reprocessing of the synthetic material.

The invention will be illustrated with reference to the following examples below.

Reference Example 1

Synthesis of β-(diethoxyphosphinyl)-ethyl-guanamine

Into a reactor were charged successively 450 g of dry dioxane, 703 g of diethyl phosphite, 282 g of acrylonitrile, and 340 g of dicyano-diamide, and the whole was cooled to 5° C. At a temperature of not more than 10° C. sodium ethanolate (prepared from 20.8 g of sodium and 196 g of dry ethanol) was added dropwise. Next, the mixture was poured into 2.5 l of demineralized water or acetone. After the whole was left to stand for one night, the white crystals were filtered off and dried. After recrystallization from water and drying the product characteristics were determined (see Table 1). The structure of the product dissolved in wholly deuterated methanol was determined via $^{13}$C-NMR and $^{1}$H-NMR. In $^{13}$C-NMR signals were observed at 169; 179; 63; 32; 24; 22; and 17 ppm. In $^{1}$H-NMR signals were observed at 4.9; 4.1; 2.25; 2.7; and 1.3 ppm.

EXAMPLE 1

Synthesis of β-(neopentylenedioxyphosphinyl)-ethyl-guanamine

In a manner analogous to that described in Reference example 1 there were charged into a reactor 225 g of freshly distilled 5,5-dimethyl-1,3,2-dioxaphosphorinane-2-oxide (boiling point 110° C. at 0.5 mm mercury pressure, melting point 55° C.), 128 g of dioxane, 80.2 g of acrylonitrile, and 101.2 g of dicyanodiamide. To the cooled mixture 63 g of sodium ethanolate solution (from 6.3 g of sodium and 57 g of dry ethanol) were added dropwise, with stirring, at a temperature below 10° C. The mixture was heated with refluxing until the mass was clear. The hot mass was poured into 350 g of demineralized water. After the whole was left to stand for one night, the crystals were filtered off, recrystallized from 1-methoxy-2-propanol, and dried. The yield was 120 g. Table 1 shows the product characteristics. The structure of the product was determined via $^{13}$C-NMR and $^{1}$H-NMR (deuteromethanol /D$_2$O). $^{13}$C-NMR signals were observed at 179; 168; 78; 35-33; 31; 22.5; and 21.5 ppm. In $^{1}$H-NMR signals were observed at 5.05; 2.75; 2.; 1.5; and 1.0 ppm.

TABLE 1

| | Example 1 | Reference example 1 |
|---|---|---|
| TLC$^{1)}$ Rf value | 0.61 | 0.63 |
| DSC (10° C./min, nitrogen) melting point(s) (°C.) | 220 | 140 and 169 |
| exothermic | | |
| start | 275 | 200 |
| peak | >300 | 280 |
| TGA (10° C./min, nitrogen) | | |
| % loss at 300° C. | 4 | 16 |
| % loss at 580° C. | 62 | 58 |
| 5% loss at °C. | 302 | 266 |
| solubility$^{2)}$ at 25° C. in acetone | <1% | <1% |
| MEK | <1% | <1% |
| 1 methoxy-2-propanol | 10% | 12% |

1)TLC (thin layer chromatography) on silica plate; mobile phase: mixture of 10 ml water, 90 ml acetone, and 25 ml n-butanol
2)weight percentages

Reference Example 2

Adducts from various molar ratios of β-(diethoxyphosphinyl)-ethyl-guanamine to the diglycidyl ether of bisphenol A (MW=380 or EEG 190, "EPIKOTE®" 828; Shell Chemicals, Houston, Tex.) were prepared in a melt, with stirring, on a 25 g scale at 150° C. The reaction was followed over time by taking samples. The gelling time of these samples on a plate (the time at which the resin comes loose from the plate) was measured at 171 ° C. under slow stirring with a wooden stick. The gelling time was found to decrease linearly with the reaction time. The adducts which were tack-free at room temperature and had a gelling time of about 5 minutes were turned, with heating, into a 65 (wt.) %-solution in 1-methoxy-2-propanol. This solution was then stored at room temperature to check whether there was precipitation of non-incorporated P-guanamine after one week. Molten adducts were also poured into aluminum cups to form 1 mm thick samples and cured in a forced-circulation air oven at 171° C. and subsequently at 200° C. The results are listed in Table 2.

TABLE 2

| molar ratio P-guanamine/ bisepoxide | % of phosphorus in resin | reaction time to gelling time of 5 minutes | clear solution | phase separation after curing |
|---|---|---|---|---|
| 0.373 | 2.4 | 85 | yes | no |
| 0.46 | 2.8 | 75 | yes | no |
| 0.53 | 3.1 | 70 | yes | no |
| 0.61 | 3.4 | 65 | no | no |
| 0.65 | 3.7 | 63 | no | yes |
| 1 | 4.7 | 55 | no | yes |

The results show that at a P-guanamine:bisepoxide molar ratio of higher than 0.60 no clear solutions or homogeneously cured products were obtained. The sample having a molar ratio of 0.46 was studied further by means of thermal analysis (see Table 3).

EXAMPLE 2

In the same way as described in Reference example 2 an adduct was prepared from β-(neopentylene dioxyphosphinyl)-ethyl-guanamine and "EPIKOTE®" 828 in a molar ratio of 0.38 and a phosphorus content of 2.4%. The reaction was carried out at 171° C. After 45 minutes the clear mass had a gelling time of 10 minutes at 171° C. The molten adduct was cured in aluminum cups in an oven at 171° C. and subsequently at 200° C.

The thermal analysis results of a sample are listed in Table 3.

Reference Example 3

In the same manner as described in Reference example 2 an adduct was prepared in the melt from benzoguanamine and "EPIKOTE®" 828 in a molar ratio of 0.52. After 70 minutes at 150° C. the gelling time was 12 minutes at 171° C. The clear molten mass was cured in aluminum cups in an oven at 171° C. and subsequently at 200° C. The thermal analysis results are listed in Table 3.

TABLE 3

|  | Example 2 | Ref. example 2 | Ref. example 3 |
|---|---|---|---|
| type of guanamine | β-(neopentylene-dioxyphosphinyl)-ethyl-guanamine | β-(diethoxy-phosphinyl)-ethyl-guanamine | benzo-guanamine |
| molar ratio guanamine/bisepoxy | 0.38 | 0.46 | 0.52 |
| DSC Tg (°C.) |  |  |  |
| heating up 1 | 120 | 102 | 113 |
| heating up 2 | 127 | 190 | 118 |
| heating up 3 | 134 | 198 | 119 |
| TGA |  |  |  |
| % loss at 300° C. | 5 | 8 | 4.5 |

EXAMPLE 3

Into a reactor were charged 406.4 g of β-(neopentylenedioxy-phosphinyl)-ethyl-guanamine, 886.8 g of 1-methoxy-2-propanol, and 923.8 g of "EPIKOTE®" 828. This mass was heated to 130° C., with stirring, and kept at this temperature for six hours until the gelling time of the 60%-resin solution was 11 minutes. Finally, the clear yellowish orange solution was cooled rapidly to room temperature, diluted with 2-methoxy-1-propanol to a 55%-solution, and stored for several weeks as a clear solution at room temperature. The phosphorus content in the solid resin was 3,3%. The viscosity of the resin solution was 407 mpa.s (measured with a Brookfield viscometer).

EXAMPLE 4

To 1 kg of the 55%-resin solution described in Example 3 MEK was added, with stirring, until a 50%-solution with a viscosity of 110 mPa.s (Brookfield viscometer) was obtained. To it were added 22 g of a 10%-solution of 2-methyl imidazole as accelerator (0.4%, calculated on the solid resin). The gelling time was 3 minutes 46 seconds at 171° C. After manual impregnation, this resin and glass cloth (style 7628) were made into prepregs in a forced-circulation air oven at 171° C. The resin content was 43%, the gelling time of the tack-free prepregs measured in accordance with IPC was 150 seconds.

Eight stacked prepregs were moulded for 60 minutes in an autoclave at a pressure of 15 atm and a temperature of 171° C. Heating and cooling took place at a rate of 5C/minute. In this way laminate coated on both sides with copper (1 ounce (28.35 g), electrodeposited type) was obtained, as well as uncoated laminate having a thickness in the range of 1.50 to 1.60 mm. The laminates were after-cured for two hours in an oven at 200° C. The properties of this laminate and of the laminate of Reference example 4 are listed in Table 4.

Reference Example 4

Into a reactor were charged 314.2 g of β-(diethoxyphosphinyl)-ethyl-guanamine, 563.2 g of 1-methoxy-2-propanol, and 1 kg of "EPIKOTE®" 828. The mass was heated to 130° C., with stirring, and kept at this temperature for four hours, until the gelling time of the 70%-resin solution had decreased to 8 minutes 50 seconds. After the addition of extra 1-methoxy-2-propanol to obtain a 58.7 (wt.) %-solution, the mass was cooled down to room temperature. After being left to stand for some days the clear mass had a viscosity of 1761 mPa.s. The phosphorus content of the solid resin was 2.7%. Analogous to Example 4, and after the addition of enough MEK to obtain a 48%-solution and 0.2% of 2-methyl imidazole (calculated on solid matter), prepregs were made in an oven from a resin having a gelling time of 205 seconds, to give prepregs having a resin content of 42% and a gelling time of 185 seconds. The preparation of laminates proceeded in the same way as in Example 4. The properties are listed in Table 4.

TABLE 4

|  | Example 4 | Ref. example 4 |
|---|---|---|
| delamination after 2 hours of after-curing at 200° C. |  |  |
| # copper coated laminate | no | yes |
| # copper-free laminate | no | no |
| DSC Tg (°C.) |  |  |
| heatingup 1 | 121 | 113 |
| heatingup 2 | 129 | 166 |
| heatingup 3 | 134 | 175 |
| TMA Tg (°C.) |  |  |
| cooling 1 | 126 | 145 |
| cooling 2 | 127 | 168 |
| cooling 3 | 131 | 172 |
| TGA |  |  |
| % foss at 300° C. | 2 | 4 |
| UL-94 | V-1 | no V classification |

We claim:

1. An adduct obtainable by condensation of a bisepoxy compound and a P-guanamine of formula:

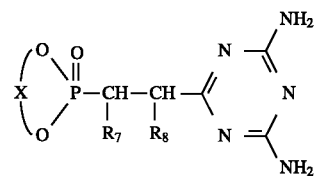

wherein X is $CR_3R_4$—$(CR_1R_2)_n$—$CR_5R_6$ or o-phenylidene, n is 0 or 1, and $R_1$–$R_8$ may be the same or different and represent H, methyl or ethyl, and the molar ratio P-guanamine: bisepoxide is 0.60 to 0.35.

2. The adduct of claim 1 wherein n is 1.

3. The adduct of claim 2 wherein $R_1$ and $R_2$ both represent a methyl group and $R_3$–$R_8$ are H.

4. The adduct of claim 1 wherein the P-guanamine is (5,5-dimethyl-2-oxo-1,3,2-dioxaphosphorinanyl)-ethyl-guanamine.

5. A resin formulation comprising the adduct of claim 1.

6. The resin formulation of claim 5 further comprising a second bisepoxy compound.

7. The resin formulation of claim 5 further comprising an additive selected from a hardener.

8. The resin formulation of claim 5 further comprising a catalyst.

9. A synthetic material comprising the adduct of claim 1.

10. A synthetic material comprising the resin formulation of claim 5.

11. A printed wiring board (PWB) comprising the adduct of claim 1.

12. A printed wiring board (PWB) comprising the resin formulation of claim 5.

13. A process for preparing the adduct of claim 1 comprising melt condensing the P-guanamine and the bisepoxy compound.

* * * * *